United States Patent [19]

Blank et al.

[11] Patent Number: 4,880,576

[45] Date of Patent: Nov. 14, 1989

[54] ACID HALIDES, A PROCESS FOR THEIR PREPARATION

[75] Inventors: Heinz U. Blank, Odanthal; Norbert Langenfeld, Cologne; Wolfgang Heydkamp, Leverkusen, all of Fed. Rep. of Germany

[73] Assignee: Bayer Aktiengesellschaft, Leverkusen, Fed. Rep. of Germany

[21] Appl. No.: 908,460

[22] Filed: Sep. 17, 1986

Related U.S. Application Data

[60] Division of Ser. No. 553,277, Nov. 17, 1983, abandoned, which is a continuation of Ser. No. 313,397, Oct. 20, 1981, abandoned.

[30] Foreign Application Priority Data

Oct. 23, 1980 [DE] Fed. Rep. of Germany ....... 3039999

[51] Int. Cl.$^4$ .................. C07C 51/60; C07C 143/70
[52] U.S. Cl. ................................ 562/828; 562/830; 562/834; 562/854; 562/855; 562/857; 562/862
[58] Field of Search ........... 260/543 R, 543 H, 544 R, 260/544 L, 544 D, 544 B, 544 K, 544 Y

[56] References Cited

U.S. PATENT DOCUMENTS

| | | | |
|---|---|---|---|
| 3,534,099 | 10/1970 | Cookson et al. | 564/215 |
| 3,894,958 | 7/1975 | McCoy et al. | 252/51.5 A |
| 4,042,621 | 8/1977 | Sauer | 564/215 |
| 4,125,724 | 11/1978 | Howell | 564/215 X |
| 4,281,193 | 7/1981 | Bellis | 564/215 |

FOREIGN PATENT DOCUMENTS

| | | |
|---|---|---|
| 2053840 | 5/1972 | Fed. Rep. of Germany . |
| 2425448 | 12/1975 | Fed. Rep. of Germany . |
| 2523633 | 12/1976 | Fed. Rep. of Germany . |

OTHER PUBLICATIONS

Journal of the American Chemical Society, Mar. 16, 1977, vol. 99, No. 6, pp. 1830–1835, Gary M. McNamee, "Electrochemical Reduction of 1-Iododecane and 1-Bromodecane at a Mercury Cathode in Dimethylformamide" (p. 1834).

Chemical Abstracts, vol. 89, No. 21, Nov. 20, 1978, p. 542, No. 179214k Radiation Chemical Addition of Dimethylformamide to Alpha-Olefins, Dederichs et al., Forsch. Technol. Kernforsch 1977, BMFT FB K 77 03, 42 pages, German.

Primary Examiner—John M. Ford
Attorney, Agent, or Firm—Sprung Horn Kramer & Woods

[57] ABSTRACT

An N-alkylated formamide of the formula

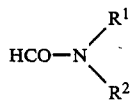

wherein
$R^1$ denotes alkyl
$R^2$ denotes alkyl with at least 9 carbon atoms or the group

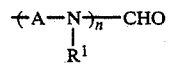

wherein
A denotes straight-chain or branched alkanediyl,
$R^1$ denotes lower alkyl and
n denotes an integer from 2 to 6, a process for the preparation of the same and its use in the replacement of a hydroxyl group in an organic compound by chlorine or bromine the improvement wherein the replacement is carried out in the presence of an N-alkylated formamide.

12 Claims, No Drawings

4,880,576

ACID HALIDES, A PROCESS FOR THEIR PREPARATION

This is a division of application Ser. No 553,277, filed Nov. 17, 1983, now abandoned, which in turn is a continuation of application Ser. No. 313,397, filed Oct. 20, 1981, now abandoned.

BACKGROUND OF THE INVENTION

Field of the Invention

The present invention relates to new N-alkylated formamides, a process for their preparation and their use as accelerators in the replacement of hydroxyl groups in organic compounds by chlorine or bromine.

SUMMARY OF INVENTION

The new N-alkylated formamides of the formula $$HCO-N\begin{matrix}R^1\\R^2\end{matrix} \quad (I)$$

in which
 $R^1$ denotes lower alkyl and
 $R^2$ denotes alkyl with at least 9 C atoms or the group $$+A-N\!\!+_n\!\!-CHO$$
$$\quad\quad\; |$$
$$\quad\quad\; R^1$$

wherein
 A denotes straight-chain or branched alkanediyl,
 $R^1$ denotes lower alkyl and
 n denotes an integer from 2 to 6
have been found.

The alkyl radicals $R^1$ are lower alkyl, for example with 1 to 4 C atoms. Such radicals can be straight-chain or branched, preferably straight-chain. Examples of these radicals are: methyl, ethyl, propyl, isopropyl, butyl and isobutyl, preferably methyl.

According to the invention, the alkyl radicals $R^2$ have at least 9 C atoms, for example 9 to 30, preferably 14-30 and particularly preferably 16 to 22, C atoms. Such alkyl radicals can be straight-chain or branched, preferably straight-chain. Examples of these radicals are: nonyl, decyl, dodecyl, myristyl, palmityl, heptadecyl, stearyl, nonadecyl, eicosyl, docosyl and triacontyl.

In the case where $R^2$ denotes the group $$+A-NR^1)_n CHO,$$

$R^1$ has the given scope of meaning,
 n denotes an integer from 2 to 6, preferably 2 to 4 and particularly preferably 2 or 3, and
 A represents straight-chain or branched alkanediyl with 2 to 8, preferably 2 to 4 and particularly preferably 2, C atoms, such as ethylene, 1,2-propylene, 1,3-propylene, 1,2-butylene, 1,3-butylene, 1,4-butylene, hexanediyl or octanediyl.

Examples of such groups are: 3,6-dimethyl-6-formyl-3,6-diaza-hexyl, 3,6-diethyl-6-formyl-3,6-diaza-hexyl, 3,6-dibutyl-6-formyl-3,6-diaza-hexyl, 3,6,9-trimethyl-9-formyl-3,6,9-triaza-nonyl, 3,6,9,12,15,18-hexamethyl-18-formyl-hexaaza-octadecyl, 2,3,5,6-tetramethyl-6-formyl-3,6-diaza-hexyl and 4,8-dimethyl-8-formyl-4,8-diaza-octyl.

Examples of the compounds according to the invention which may be mentioned are: N-nonyl-, N-decyl-, N-dodecyl-, N-myristyl-, N-palmityl-, N-heptadecyl-, N-stearyl-, N-nonadecyl-, N-eicosyl-, N-docosyl- and N-tricontyl-methylformamide, -ethylformamide, -propylformamide and -butylformamide, and $\alpha,\omega$-bisformyl-N,N',N''-trimethyl-diethylenetriamine, $\alpha,\omega$-bisformyl-N,N',N'',N'''-tetramethyl-triethylenetetramine and $\alpha,\omega$-bisformyl-N,N',N'',N''',N^{IV},N^V,N^{VI}$-heptamethyl-hexaethylene-heptamine, and $\alpha,\omega$-bisformyl-N,N',N''-trimethyl-di-1,2-propylene-triamine.

Preferred compounds within the scope of the formula (I) are those of the formula $$HCO-N\begin{matrix}R^3\\R^4\end{matrix} \quad (II)$$

in which
 $R^3$ denotes $C_1$–$C_4$-alkyl and
 $R^4$ denotes $C_{14}$–$C_{30}$-alkyl.

Particularly preferred compounds within the scope of the formula (I) are those of the formula $$HCO-N\begin{matrix}CH_3\\R^5\end{matrix} \quad (III)$$

in which
 $R^5$ denotes $C_{16}$–$C_{22}$-alkyl.

Further preferred compounds within the scope of the formula (I) are those of the formula $$\begin{matrix}R^3 & R^3\\| & |\\HCO-N+B-N+_m CHO\end{matrix} \quad (IV)$$

in which
 $R^3$ denotes $C_1$–$C_4$-alkyl,
 B denotes straight-chain or branched $C_2$–$C_4$-alkanediyl and
 m denotes an integer from 2 to 4, Further particularly preferred compounds within the scope of the formula (I) are those of the formula $$\begin{matrix}CH_3 & CH_3\\| & |\\HCO-N+B-N+_o CHO\end{matrix} \quad (V)$$

in which
 o denotes the number 2 or 3 and
 B has the meaning given.

Very particularly preferred compounds within the scope of the formula (V) are those of the formula $$HCO-NCH_3+CH_2-CH_2-NCH_3+_o CHO \quad (VI)$$

in which
 o has the meaning given.

The invention furthermore relates to mixtures of substances of the formula (I), in particular mixtures of substances of the formula (IV) or of the formula (V). These mixtures can consist of 2 or more substances of the formulae given, preferably of 2 to 6 substances and particularly preferably of 2 to 4 substances.

Furthermore, a process has been found for the preparation of the N-alkylated formamides of the formula $$HCO-N\diagup^{R^1}_{\diagdown R^2} \qquad (I)$$

in which
R$^1$ denotes lower alkyl and
R$^2$ denotes alkyl with at least 9 C atoms or the group $$+A-N\overline{)_n}CHO,$$
$$\phantom{+A-N}|$$
$$\phantom{+A-N}R^1$$

wherein
A denotes straight-chain or branched alkanediyl,
R$^1$ denotes lower alkyl and
n denotes an integer from 2 to 6,
which is characterised in that N-alkylated amines of the formula $$HN\diagup^{R^1}_{\diagdown R^6} \qquad (VII)$$

in which
R$^1$ has the meaning given and
R$^6$ denotes alkyl with at least 9 C atoms or the group $$+A-N\overline{)_n}H,$$
$$\phantom{+A-N}|$$
$$\phantom{+A-N}R^1$$

wherein
A denotes straight-chain or branched alkanediyl,
R$^1$ denotes lower alkyl and
n denotes an integer from 2 to 6,
are reacted with formic acid at elevated temperature, if desired in the presence of an inert solvent.

The substituents of the N-alkylated amines which can be employed according to the invention have the abovementioned scope of meaning. Examples of such N-alkylated amines are: N-nonyl-, N-decyl-, N-dodecyl-, N-myristyl-, N-palmityl-, N-heptadecyl-, N-stearyl-, N-nonadecyl-, N-eicosyl-, N-docosyl- and N-tricontyl-methylamine, -ethylamine, -propylamine and -butylamine, and N,N',N''-triethyl-diethylene-triamine, and N,N',N'',N''',N$^{IV}$,N$^V$,N$^{VI}$-heptamethyl-hexaethylene-heptamine, and N,N',N''-trimethyl-di-1,2-propylene-triamine.

Preferably, N-alkylated amines of the formula $$HN\diagup^{R^3}_{\diagdown R^4} \qquad (VIII)$$

and particularly preferably those of the formula $$HN\diagup^{CH_3}_{\diagdown R^5} \qquad (IX)$$

in which
R$^3$, R$^4$ and R$^5$ have the abovementioned scope of meaning,
are employed in the process according to the invention.

Further N-alkylated amines which can preferably be employed in the process according to the invention are those of the formula $$\begin{array}{cc}R^3 & R^3\\|& |\\HN+B-N\overline{)_m}H\end{array} \qquad (X)$$

and further amines which can particularly preferably be employed are those of the formula $$HNCH_3+B-NCH_3\overline{)_o}H$$
(XI)

and, within the scope of the formula (X), amines which can very particularly preferably be employed are those of the formula $$HNCH_3+CH_2-CH_2-NCH_3\overline{)_o}H$$
(XII)

wherein
R$^3$, B, m and o have the abovementioned meaning.

N-Alkylated amines of the formulae (VII) to (XII) are known to the expert. In the case where R$^6$ and the radicals R$^4$ and R$^5$ derived therefrom denote alkyl with at least 14 C atoms, such amines can be obtained, for example, by reacting α-halogeno-paraffins or primary alcohols with mono-lower alkyl-amines (Houben-Weyl, Methoden der organischen Chemie (Methods of Organic Chemistry), Volume XI/1, pages 40 and 120, Georg Thieme Verlag 1957). In the case where R$^6$ represents the group —A—NR$^1$)$_n$H, and in the case of the derived formulae (X), (XI) and (XII), such polyamines can be obtained by reacting dihalogenoalkanes, in which the C-chain can be straight-chain or branched, with mono-lower alkylamines (Chem. Ber. 94, 831–833 (1961)). In the case where mixtures of substances of the formulae (I), (IV), (V) or (VI) are to be obtained according to the invention, it is, of course, possible to employ mixtures of the amines mentioned and/or polyamines of the formulae (VII), (X), (XI) or (XII) in the process according to the invention. This procedure is preferred if, for example, a mixture of α-halogenoparaffins of different chain lengths is used as the starting material in the industrial preparation of the amines to be employed, or if, for example, the reaction of the dihalogenoalkanes with alkylamines leads to a mixture of polyamines with different numbers of N atoms, and the industrial mixtures thus obtained cannot be separated into the individual components for reasons of cost.

According to the invention, the N-alkylated amine and the formic acid are employed in a molar ratio of 1:1 to 20, preferably 1:1 to 5, and particularly preferably 1:1 to 1.5, relative to each N atom which can be acylated.

A reaction temperature which may be mentioned by way of example is 50° to 150° C. The reaction of the process according to the invention is preferably carried out at the boiling point of the reaction mixture.

The reaction can be carried out under normal pressure or under increased or reduced pressure. It is preferably carried out under normal pressure or under reduced pressure, for example in the range from 1 to 1,000 mbars, preferably under 50–1,000 mbars.

To improve the yield by enabling the reaction of the process according to the invention to go further towards completion, the water formed in the reaction can be removed during the reaction. This can be effected, for example, by applying elevated temperature and/or reduced pressure and distilling off the water of reaction, by means of agents which remove water, or by entraining the water of reaction out of the reaction mixture by azeotropic distillation using a suitable entraining agent. A preferred variant is that of removal of the water by azeotropic distillation. In this case, the reaction according to the invention is carried out in the presence of a solvent which does not undergo side-reactions with the reactants under the reaction conditions and which is water-immiscible or miscible with water only to a limited extent, but forms an azeotrope with water. Solvents which may be mentioned in this context are aliphatic or aromatic hydrocarbons, such as benzene, toluene, ethylbenzene, isopropylbenzene, o-, m- and p-xylene or hexane, and aliphatic or aromatic halogenated hydrocarbons, such as chlorobenzene, o-, m- and p-dichlorobenzene or dichloroethane. Toluene is the preferred solvent for the process according to the invention, which forms an azeotrope with water.

It is, of course, also possible for other inert solvents which do not form an azeotrope with water to be employed in the process according to the invention. All the solvents mentioned which do or do not form an azeotrope can be employed either individually or as a mixture. It is preferable to use only one solvent, which forms an azeotrope, toluene being particularly preferred.

A further preferred variant is the reaction of the amine with formic acid in the absence of a solvent, the water of reaction formed being removed by means of elevated temperature, if necessary under reduced pressure.

The reaction product can be isolated, for example, by distilling off the solvent which may have been used and, if appropriate, excess reactants. The product thus obtained is in most cases sufficiently pure for further use. If a product which has been purified further is desired, purification can be effected by known processes, for example by distillation, extraction, recrystallization or chromatography.

It is, of course, also possible to use other preparation methods for formylated amines for the preparation of the N-alkylated formamides of the formula (I). Such methods are described, for example, in Houben-Weyl, Methoden der organischen Chemie (Methods of Organic Chemistry), 4th edition, 1958, volume XI/2, pages 27 to 30, and include, for example, the reaction of N-alkylated amines of the formula (IV) with ammonium formate, a mixture of formic acid and acetic acid, alkyl formates, formamide, formyl fluoride, chloral or carbon monoxide.

The N-alkylated formamides according to the invention can be used as accelerators in the replacement of hydroxyl groups in organic compounds by chlorine or bromine. They can furthermore be used as accelerators in the reaction of phenolic compounds with phosgene to give aryl chloroformates.

The N-alkylated formamides of the invention when used as accelerators are employed in a reaction mixture in an amount of between 0.01 and 100 mol percent, preferably between 0.1 and 50 mol percent. This includes in particular those processes wherein said N-alkylated formamides are employed in the replacement of hydroxyl groups in organic compounds by chlorine or bromine, in the reaction of organic acids or their salts with an inorganic acid chloride or bromide to form the corresponding organic acid chloride or bromide or in the reaction of phenolic compounds with phosgene to form aryl chloroformates.

An example which may be mentioned of a process for the replacement of hydroxyl groups in organic compounds by chlorine or bromine which can be accelerated by the N-alkylated formamides according to the invention is the preparation of N-heterocyclic compounds which have at least 1 halogen atom in the α-position relative to the hetero-nitrogen, from the corresponding N-heterocyclic compounds which carry at least one hydroxyl group in the α-position and an inorganic acid halide. The said replacement on aromatic N-heterocyclic compounds may be mentioned in particular. This reaction can be represented by the following general equation:

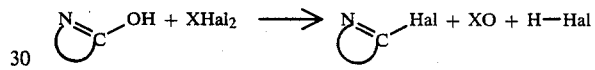

wherein
Hal represents chlorine or bromine, preferably chlorine, and
X represents CO, SO or $SO_2$,
and wherein the curved connecting line between N and C denotes the heterocyclic ring, which optionally also contains a replaceable hydroxyl group on the second α-position relative to the N atom, this reaction being carried out in the presence of the substances of the formula (I) according to the invention.

Suitable starting substances for the mentioned process are heterocyclic compounds which carry at least one hydroxyl group in the α-position relative to a ring nitrogen atom, or tautomeric forms of these compounds. The heterocyclic compounds can also carry several hydroxyl groups in the α-position relative to a ring nitrogen atom. The heterocyclic compounds can furthermore also contain several ring nitrogen atoms, which in turn have hydroxyl groups in the α-position. Such heterocyclic compounds can be derived, for example, from the following heterocyclic ring systems: pyridine, 1,2-, 1,3- and 1,4-diazine, 1,2,5- and 1,3,5-triazine, tetrazines, tetrazoles, quinoline, isoquinoline, quinoxaline, quinazoline and phthalazine. In addition to the hydroxyl substituents mentioned, these ring systems can also contain one or more of the following substituents, which, where appropriate, are likewise converted into the chlorides under the conditions according to the invention: examples which may be mentioned are the carboxylic acid group or the sulphonic acid group.

The heterocyclic compounds which can be employed according to the invention can, of course, carry substituents which are not changed under the chlorination conditions, such as lower alkyl, halogens, such as fluorine, chlorine or bromine, lower alkoxy, cyano, nitro and lower halogenoalkyl.

Starting substances for the process according to the invention are preferably derived from the following ring systems: quinoline, isoquinoline, quinoxaline, quinazoline and phthalazine. Derivatives of quinoxaline are particularly preferred as the starting substances.

Examples of individual compounds which can be employed, according to the invention, as starting substances are: 2-hydroxypyridine, 2,3- and 2,5-dihydroxypiperazine, 2-hydroxy-4,6-dimethylpyrimidine, 4-hydroxy-2,6-dimethylpyrimidine, 2,4-dihydroxy-6-methylpyrimidine, 2-phenyl-4,6-dihydroxytriazine, 2-hydroxyquinoline, 2,4-dihydroxyquinazoline, 6-chloro-2,4-dihydroxyquinazoline, 2,3-dihydroxy-quinoxaline, 6-chloro-2,3-dihydroxyquinoxaline, 6-methyl-2,3-dihydroxy-quinoxaline, 6,7-dimethoxy-2,3-dihydroxyquinoxaline, 2,3-dihydroxyquinoxaline-6-carboxylic acid, 2,3-dihydroxy-5-methylquinoxaline, 2,3-dihydroxy-6,7-dimethyl-quinoxaline and 2,3-dihydroxyquinoxaline-5-carboxylic acid.

A further example which may be mentioned of the replacement of a hydroxyl group in organic compounds by chlorine or bromine is the preparation of organic acid chlorides or bromides, such as carboxylic acid chlorides, carboxylic acid bromides, sulphonic acid chlorides or sulphonic acid bromides, from the acids or their salts and an inorganic acid chloride or acid bromide. These reactions can be described, for example, by the following general equation:

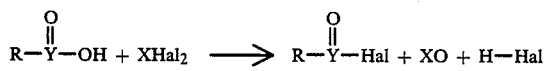

wherein
X and Hal have the abovementioned meaning,
R represents alkyl, cycloalkyl, aralkyl, aryl or heteroaryl, it furthermore being possible for R to be substituted by alkyl, cycloalkyl, aryl, hetero-aryl, halogen, alkoxy, aryloxy, nitro or cyano or by one or more carboxylic acid or sulphonic acid groups, which, if appropriate, are also converted into acid halide groups, and
Y represents a C atom or the SO group,
the substances of the formula (I) according to the invention being employed as accelerators in these reactions.

Compounds which can be obtained hereby are e.g., chloro acetic acid chloride, dichloro acetic acid chloride, benzoic acid chloride, o-, m- and p-chloro benzoic acid chloride, o-, m- and p-methyl benzoic acid chloride, o-methoxy benzoic acid chloride, terephthalic acid dichloride, isoterephthalic acid dichloride, benzene sulfonic acid chloride, o-, m- and p-toluene sulfonic acid chloride, o-, m- and p-chlorobenzene sulfonic acid chloride and α- and β-naphthalene sulfonic acid chloride.

The abovementioned reaction of phenolic compounds with phosgene to give aryl chloroformates, which can likewise be accelerated by the substances of the formula (I) according to the invention, may be characterized, for example, by the following equation:

Ar—OH+COCl₂→Ar—O—CO—Cl+HCl wherein
Ar represents an aryl radical, for example phenyl, naphthyl or anthryl, which can optionally carry further substituents, as disclosed for R.

The invention thus furthermore relates to the use of the N-alkylated formamides of the formula (I) for accelerating the replacement of hydroxyl groups in organic compounds by chlorine or bromine, in particular for accelerating the replacement of hydroxyl groups in the α-position in N-heterocyclic compounds and the OH groups contained in organic acids, acid halide groups being formed. The invention likewise relates to the use of the N-alkylated formamides of the formula (I) for accelerating the reaction of phenolic compounds with phosgene to give aryl chloroformates.

Compounds which can be obtained hereby are e.g. chloroformic acid phenyl ester, p-chlorophenyl ester, α-naphthyl ester and β-naphthyl ester.

In addition to the pure substances of the formula (I), it is, of course, also possible for mixtures of such substances to be employed according to the invention. The advantageous properties of the pure substances with respect to their complete catalytic activity and the properties from the point of view of work hygiene are retained in their entirety in such mixtures.

Dialkylformamides in which the alkyl radicals have at most 4 C atoms, in particular dimethylformamide, have hitherto been used as catalysts for such reactions (DE-AS (German Published Specification) 1,178,052; and Helv. Chim. Acta. 42, 1,653 to 1,658 (1959)). However, it has since been disclosed that N,N-dialkylcarbamoyl chlorides are formed from dimethylformamide and thionyl chloride or phosgene, which are frequently employed for the replacement of an OH group by chlorine (Isv. Akad. Nauk USSR, Chem. Ser. 1971 (3), 513-519; quoted in C.A. 75, 48,340m). These carbamoyl chlorides have proved to be carcinogenic in animal experiments (J. Nat. Cancer Inst. 48 (5), 1,539–1,541 (1972); quoted in C.A. 77, 97,540b). The N,N-dialkylformamides with lower alkyl radicals, in particular dimethylformamide, are thus unacceptable for reasons of work hygiene, so that it appears necessary to replace them.

When the N-alkylated formamides of the formula (I) according to the invention are used, they do not pass into the environment, or pass into the environment only to a negligible extent, so that their use provides advantages from the point of view of work hygiene. Surprisingly, they prove to be completely active as catalysts, although in the Deutsche Auslegeschrift 1,178,052 mentioned, the catalytically active alkylformamides are restricted to those with short-chain alkyl radicals with up to 4 C atoms.

EXAMPLE 1

Preparation of N-methyl-stearylformamide 500 ml of toluene are initially introduced into a 2 liter three-necked flask with a stirrer, internal thermometer and water separator. 566 g of N-methylstearylamine (99% pure) and then 97 g of formic acid (99% pure) are added at room temperature. The mixture is then heated to the boiling point until no further water is separated off. The product mixture is freed from toluene in a rotary evaporator under 30 mbars and at a bath temperature of up to 80° C.

630 g of N-methylstearylformamide with a content, determined by gas chromatography, of 97% are recovered as the distillation residue.

Melting point: 34° C.
Boiling point: 185° C./1 mbar, with decomposition
Yield: 99% of the theoretical yield

EXAMPLE 2

227 g of 2,3-dihydroxyquinoxaline-6-carboxylic acid with a content of 91% are initially introduced into a 1 liter three-necked flask which is equipped with a stirrer, internal thermometer and reflux condenser, to which a bubble counter and gas outlet are attached. 785 g of thionyl chloride and 18.6 g of N-methyl-stearylformamide are then added at room temperature. The batch is heated to the boiling point, whereupon vigorous evolution of gas starts. The boiling point rises from about 55° C. to 79° C. during the reaction. After about 5 hours, the suspension has become a solution, and after a further 1-2 hours the reaction has ended, which can be recognized by the end of the evolution of gas. Excess thionyl chloride is distilled off, first under normal pressure and then under 20 mbars, up to a bottom temperature of 120° C. 130 g of thionyl chloride are recovered.

The liquid residue is poured onto a metal sheet and, after cooling, the product is pulverized in a mortar. 276 g of 2,3-dichloroquinoxaline-6-carboxylic acid chloride are isolated. The product has a content, determined by sublimation, of 94%. The yield is 99% of the theoretical yield.

Content of N-methyl-N-stearyl-carbamoyl chloride: (a) not detectable in the gas space above the hot product; and (b) not detectable in the thionyl chloride recovered.

EXAMPLE 3

283.5 g (3.0 mols) of chloroacetic acid and 4.67 g (0.015 mol) of N-methyl-stearylformamide are initially introduced, at 90° C., into a four-necked flask with a stirrer, internal thermometer, gas inlet tube and reflux condenser, the upper end of which is connected to a phosgene destruction tower via two wash bottles.

400 g of phosgene are passed in below the surface of the starting material through the inlet tube in the course of 7 hours, until the reaction has ended (recognisable by the subsiding of the evolution of gas and by the fall in temperature). The mixture is subsequently stirred at the reaction temperature for a further hour. Excess phosgene is then blown out with nitrogen at 90° C. for 1 hour.

The product is distilled at an overhead temperature of 105° C.

Main runnings: 298 g of chloroacetyl chloride (88% of the theoretical yield).

First runnings of 5 g can be passed to the subsequent batch. The product contains less than the detection limit of 1 ppm of N-methyl-stearyl-carbamoyl chloride in chloroacetyl chloride.

EXAMPLE 4

Analogously to Example 3, 386.7 g (3.0 mols) of dichloroacetic acid and 4.67 g (0.015 mol) of N-methyl-stearylformamide are reacted with 500 g of phosgene in the course of 10.5 hours and the mixture is worked up. Overhead temperature during the distillation: 108°-109° C. Main runnings: 375 g of dichloroacetyl chloride (85% of the theoretical yield).

First runnings of 13 g can be passed to the subsequent batch. The product contains less than the detection limit of 1 ppm of N-methyl-stearyl-carbamoyl chloride in dichloroacetyl chloride.

EXAMPLE 5

Analogously to Example 3, 238 g (1.75 mols) of o-methylbenzoic acid and 2.75 g (0.009 mol) of N-methyl-stearylformamide are reacted with 215 g of phosgene at 100°-105° C. in the course of 4 hours and the mixture is worked up.

Distillation is carried out under 20 mbars and at an overhead temperature of 102° C.

Main runnings: 262 g of o-methylbenzoyl chloride (97% of the theoretical yield).

First runnings of 5 g can be passed to the subsequent batch. The product contains less than the detection limit of 100 ppm of N-methyl-stearyl-carbamoyl chloride in o-methylbenzoyl chloride.

EXAMPLE 6

Analogously to Example 3, 190 g (1.22 mols) of o-methoxybenzoic acid and 3.8 g (0.012 mol) of N-methyl-stearylformamide are reacted with 200 g of phosgene at 100°-105° C. in the course of 3.5 hours and the mixture is worked up.

Distillation is carried out under 20 mbars and at an overhead temperature of 142° C.

Main runnings: 199 g of o-methoxybenzoyl chloride (93% of the theoretical yield).

No first runnings are obtained. The product contains less than the detection limit of 50 ppm of N-methyl-stearycarbamoyl chloride in o-methoxybenzoyl chloride.

EXAMPLE 7

Analogously to Example 3, 188 g (1.2 mols) of m-chlorobenzoic acid and 3.73 g (0.012 mol) of N-methyl-stearylformamide are reacted with 220 g of phosgene at 110° C. in the course of 5.5 hours and the mixture is worked up.

Distillation is carried out under 20 mbars and at an overhead temperature of 110° C.

Main runnings: 201 g of m-chlorobenzoyl chloride (96% of the theoretical yield).

First runnings of 4 g can be passed to the subsequent batch. The product contains 35 ppm of N-methyl-stearylcarbamoyl chloride.

EXAMPLE 8

Analogously to Example 3, 188 g (1.2 mols) of p-chlorobenzoic acid and 3.73 g (0.012 mol) of N-methyl-stearylformamide are reacted with 220 g of phosgene at 110° C. in the course of 3.5 hours and the mixture is worked up.

Distillation is carried out under 20 mbars and at an overhead temperature of 109° C.

Main runnings: 196.5 g of p-chlorobenzoyl chloride (94% of the theoretical yield).

First runnings of 4 g can be passed to the subsequent batch. The product contains 18 ppm of N-methyl-stearylcarbamoyl chloride.

EXAMPLE 9

This example is carried out as Example 8, using the following amounts and with the following results: 476 g (3.5 mols) of m-methylbenzoic acid, 5.5 g (0.016 mol) of N-methylstearylformamide and 430 g of phosgene; at 104°-110° C. in the course of 5½ hours; distillation at 90°-92°/16 mbars; yield: 528 g of main runnings (97.6% of the theoretical yield) and <2 g of first runnings.

The product contains less than 100 ppm of methyl-stearyl-carbamoyl chloride, which is less than the detection limit in m-methylbenzoyl chloride.

EXAMPLE 10

500 g of phenol and 33.1 g of N-methyl-stearylformamide are initially introduced into a four-necked flask with a stirrer, internal thermometer, gas inlet tube and a reflux condenser which is charged with dry ice and is connected to a phosgene destruction tower.

550 g of phosgene are then passed in at 120°–125° C. in the course of 12 hours. Excess phosgene is stripped off. The product is distilled under a waterpump vacuum.

Main fraction at 80°–82° C./20 mbars; 727.5 g (99.7% pure); last runnings: 108.2 g (34.4% pure).

Yield of phenyl chloroformate: 91% of the theoretical yield.

The product contains 4 ppm of N-methylstearylcarbamoyl chloride.

EXAMPLE 11

136.2 g (1 mol) of o-methylbenzoic acid and 3.1 g (0.01 mol) of N-methylstearylformamide are initially introduced into an apparatus such as is described in Example 10. 130 g of phosgene are passed in at 100° C. in the course of 4 hours. After stripping off the excess phosgene, the product is distilled using an oil pump (2–3 mbars, 66° C.).

Main runnings: 149.5 g of o-methylbenzoyl chloride (97% of the theoretical yield).

The product contains less that the detection limit of 100 ppm of N-methylstearylcarbamoyl chloride in o-methylbenzoyl chloride.

EXAMPLE 12

166.2 g (1 mol) of isophthalic acid and 297.5 g (2.5 mols) of thionyl chloride are heated under reflux with 1 g (0.003 mol) of N-methylstearylformamide for 4 hours in a three-necked flask with a stirrer, internal thermometer and reflux condenser. Excess thionyl chloride is distilled off under 30 mbars, up to a bottom temperature of 100° C. 202.4 g of isophthaloyl chloride with a content of 98% remain as the residue. Yield: 97.7% of the theoretical yield.

EXAMPLE 13 (Comparison to Example 6)

This example is carried out as Example 6, using the following amounts and with the following results: 190 g (1.22 mols) of o-methoxybenzoic acid, 0.74 g (0.01 mol) of dimethylformamide and 200 g of phosgene; yield: 206 g of main runnings.

The product contains about 400 ppm of dimethylcarbamoyl chloride.

EXAMPLE 14 (Comparison to Examples 5 and 11)

This example is carried out as Example 3, using the following amounts and with the following results: 476 g (3.5 mols) of m-methylbenzoic acid, 2.56 g (1.0 mol%) of dimethylformamide and 430 g of phosgene; at 100°–110° C. in the course of 5 hours; distillation at 90°–92°/16 mbars; yield: 534 g of main runnings and 3 g of first runnings.

1,100 ppm of dimethylcarbamoyl chloride can be detected in the main runnings and 1,500 ppm of dimethylcarbamoyl chloride can be detected in the first runnings.

EXAMPLE 15

300 ml of toluene are initially introduced into a 500 ml three-necked flask with a stirrer, internal thermometer and water separator. 70.5 g of N,N',N''-trimethyl-diethylenetriamine (89% pure) are introduced at room temperature and 67 g of formic acid (99% pure) are then added.

The reaction and the distillation of the toluene are carried out as in Example 1.

The evaporation residue is distilled in vacuo.

88 g of α,ω-bisformyl-N,N',N''-trimethyl-diethylenetriamine with a content of 97% are obtained as the main fraction.

Boiling point: 182°–185° C./1.3 mbars.

Yield: 98% of the theoretical yield.

EXAMPLE 16

Analogously to Example 2, 113.2 g of 2,3-dihydroxyquinoxaline-6-carboxylic acid with a content of 91% are reacted with 393 g of thionyl chloride in the presence of 4.6 g of α,ω-bis-formyl-N,N',N''-trimethyldiethylenetriamine in a 0.5 l three-necked flask and the mixture is worked up.

99 g of thionyl chloride are recovered.

135 g 2,3-dichloroquinoxaline-6-carboxylic acid chloride with a content, determined by sublimation, of 88% are isolated. The yield is 91% of the theoretical yield.

No carbamoyl compound corresponding to the catalyst could be detected.

EXAMPLES 17–19

The following formamides are prepared analogously to Example 1:

| Example | Formamide | Boiling point | Yield |
|---------|-----------|---------------|-------|
| 1 a | N—methyltetradecyl-formamide | 130° C./0.3 mbar | 98% |
| 1 b | N—methylhexadecyl-formamide | 165°/0.4 mbar | 99% |
| 1 c | N—ethylstearyl-formamide | 190° C./0.4 mbar | 99% |

EXAMPLE 20

1,013 g of N-methylstearylamine are initially introduced, at 105° C., into a 2 liter flask with a stirrer, internal thermometer, Vigreux column and distillation device. 173.6 g of formic acid are added dropwise at 105° C. in the course of one hour. After a further hour at 105° C., the mixture is then heated to 120° C. in the course of 1½ hours, during which about 41 g of water are distilled off. A further 15 ml of water are distilled off by gradually applying a vacuum of 8 mbars. The mixture is subsequently stirred for a further hour at 120° C./8 mbars. 1,109 g of methylstearylformamide (97.2% pure) remain as the residue.

Yield: 99% of the theoretical yield

Melting point: 33°–34° C.

EXAMPLE 21

476 g (3.50 mols) of m-methylbenzoic acid and 3.5 g of α,ω-bis-formyl-N,N',N''-trimethyl-diethylenetriamine are reacted with 565 g of phosgene at 104°–108° C. in the course of 7 hours in a stirred apparatus with a gas inlet tube, thermometer and reflux condenser which is connected to a phosgene destruction tower via a safety gas-bottle.

The crude product is freed from phosgene by stirring at 110° C. in a stream of nitrogen for one hour. Distillation at 102°–104° C./27 mbars gives 528 g of colourless m-methylbenzoyl chloride (97.6% of the theoretical yield) with a content of over 99.6%.

The carbamoyl chloride corresponding to the catalyst cannot be detected (detection limit: 20 ppm).

EXAMPLE 22

190 g (1.24 mols) of o-methoxybenzoic acid and 2.5 g of α,ω-bis-formyl-N,N',N''-trimethyl-diethylenetriamine are reacted with 230 g of phosgene at 100°–108° C. in the course of 4 hours in the abovementioned apparatus.

After removal of the phosgene and distillation, 198.6 g of colourless o-methoxybenzoyl chloride (93% of the theoretical yield) are formed.

Content: greater than 99.6%.

The carbamoyl chloride corresponding to the catalyst cannot be detected (detection limit: 100 ppm).

What is claimed is:

1. In a process for preparing an organic acid chloride from the corresponding acid or a salt thereof by contacting said acid or salt thereof with an inorganic acid halide, the improvement which comprises carrying out the process in the presence of an N-alkylated formamide of the formula

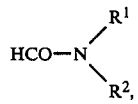

wherein
$R^1$ is alkyl with 1 to 4 carbon atoms,
$R^2$ is alkyl with at least 9 carbon atoms or the group

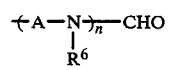

wherein
A is straight-chain or branched alkanediyl,
$R^6$ is lower alkyl and
n is an integer from 2 to 6, wherein said inorganic acid halide has the formula $XHal_2$, wherein Hal is chlorine and X is selected from the group consisting of CO, SO and $SO_2$ and wherein the organic acid chloride is selected from the group consisting of chloro acetic acid chloride, dichloro acetic acid chloride, benzoic acid chloride, o-chloro benzoic acid chloride, m-chloro benzoic acid chloride, p-chloro benzoic acid chloride, o-methoxy benzoic acid chloride, terephthalic acid dichloride, isoterephthalic acid dichloride, benzene sulfonic acid chloride, o-toluene sulfonic acid chloride, m-toluene sulfonic acid chloride, p-toluene sulfonic acid chloride, o-chlorobenzene sulfonic acid chloride, m-chlorobenzene sulfonic acid chloride, p-chlorobenzene sulfonic acid chloride, alpha-naphthalene sulfonic acid chloride and beta-naphthalene sulfonic acid chloride.

2. A process according to claim 1, wherein
$R^1$ is $C_1$–$C_4$-alkyl and
$R^2$ is straight-chain $C_{14}$–$C_{30}$-alkyl.

3. A process according to claim 1, wherein the N-alkylated formamide is of the formula

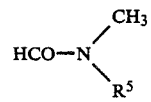

wherein
$R^5$ is $C_{16}$–$C_{22}$-alkyl.

4. A process according to claim 1, wherein the N-alkylated formamide is of the formula

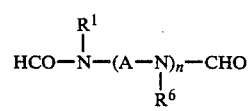

wherein
$R^6$ denotes $C_1$–$C_4$-alkyl,
A denotes straight-chain or branched $C_2$–$C_4$-alkanediyl and
n denotes an integer from 2 to 4.

5. A process according to claim 1, wherein the N-alkylated formamide of the formula

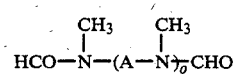

wherein
o is the number 2 or 3 and
A is straight-chain or branched $C_2$–$C_4$-alkanediyl.

6. A process according to claim 1, wherein $R^1$ is methyl and $R^2$ is stearyl.

7. A process according to claim 1, wherein $R^1$ is methyl and $R^2$ is tetradecyl.

8. A process according to claim 1, wherein $R^1$ is methyl and $R^2$ is hexadecyl.

9. A process according to claim 1, wherein $R^1$ is ethyl and $R^2$ is stearyl.

10. A process according to claim 1, wherein the N-alkylated formamide is α,ω-bis-formyl-N,N',N''-trimethyl-diethylenetriamine.

11. A process according to claim 1, wherein
$R^1$ is an alkyl radical selected from the group consisting of ethyl and methyl and
$R^2$ is straight-chain $C_{14}$ to $C_{22}$ alkyl.

12. A process according to claim 1, wherein $R^1$ is methyl.

* * * * *